United States Patent [19]

Moore et al.

[11] Patent Number: 5,049,670
[45] Date of Patent: * Sep. 17, 1991

[54] PERFLUOROAMINOETHERS

[75] Inventors: George G. I. Moore, Afton; John C. Hansen, Lakeland, both of Minn.

[73] Assignee: Minnesota Mining and Manufacturing Company, St. Paul, Minn.

[*] Notice: The portion of the term of this patent subsequent to May 29, 2007 has been disclaimed.

[21] Appl. No.: 482,829

[22] Filed: Feb. 21, 1990

Related U.S. Application Data

[60] Division of Ser. No. 236,033, Aug. 24, 1988, Pat. No. 4,927,725, which is a division of Ser. No. 894,311, Aug. 14, 1986, Pat. No. 4,788,339, which is a continuation-in-part of Ser. No. 773,314, Sep. 16, 1985, abandoned.

[51] Int. Cl.$^5$ ............... C07D 265/30; C07D 211/22; C07D 207/09
[52] U.S. Cl. .................................. 544/87; 544/357; 546/186; 546/191; 548/215; 548/300; 548/523
[58] Field of Search ............... 544/87, 357; 546/186, 546/191; 548/215, 300, 523

[56] References Cited

U.S. PATENT DOCUMENTS

| | | | |
|---|---|---|---|
| 2,519,983 | 8/1950 | Simons | 204/62 |
| 2,567,011 | 9/1951 | Diesslin et al. | 260/465.7 |
| 2,713,593 | 7/1955 | Brice et al. | 260/535 |
| 2,882,182 | 5/1975 | Benninger et al. | 260/584 |
| 3,028,321 | 4/1962 | Danielson et al. | 204/59 |
| 3,274,081 | 9/1966 | Pearlson | 204/59 |
| 3,882,178 | 5/1975 | Benninger et al. | 260/563 |
| 3,891,625 | 6/1975 | Benninger et al. | 260/239 |
| 3,997,609 | 12/1976 | Martini et al. | 260/584 |
| 4,929,725 | 5/1990 | Moore et al. | 544/87 |

OTHER PUBLICATIONS

J. Fluorine Chem. 27, 333 (1985), T. Ono et al.
Tetrahedron Letters, pp. 3251-3254 (1975), H. H. Freedman and R. A. Dubois.
Sokolov, S. V. et al., "Methods of Preparation and Properties of Organofluorine Compounds: V. Values of Chemical Shifts in NMR Spectra of Perfluorinated Nitrogen-Containing Heterocyclic Compounds," *Journal of General Chemistry of the USSR*, vol. 36, No. 9, Sep. 1966, pp. 1615-1619.

*Primary Examiner*—Richard L. Raymond
*Attorney, Agent, or Firm*—Gary L. Griswold; Walter N. Kirn; Carole Truesdale

[57] ABSTRACT

Perfluoroaminoethers are provided. The perfluoroaminoiethers have two or more tertiary amino nitrogen atoms each of which is connected to the other(s) adjacent thereto by (1) a catenary, ether oxygen-containing, perfluoroalkylene linking group the catenary carbon atoms of which are in the form of segments of vicinal carbon atoms that are 2 to 4 in number, said segments having up to 5 carbon atoms, a catenary ether oxygen-containing perfluorocyclohexylene linking group, or (3) a catenary ether oxygen-containing linking group having perfluoroalkylene and perfluorocyclohexylene moieties, the sum of the catenary ether oxygen atoms being 1 to 6.

9 Claims, No Drawings

PERFLUOROAMINOETHERS

This application is a division of application Ser. No. 236,033 filed Aug. 24, 1988, now U.S. Pat. No. 4,929,725, which is a division of application Ser. No. 894,311 filed Aug. 14, 1986, now U.S. Pat. No. 4,788,339, which is a continuation-in-part of application Ser. No. 773,314, filed Sept. 6, 1985, now abandoned.

This invention relates to perfluorinated aminoether compositions and to their preparation by electrochemical fluorination of precursor aminoether compounds.

Perfluorinated trialkylamines prepared by electrochemical fluorination are known inert fluids and although useful for many applications do not have a sufficiently low pour point for some low temperature uses. Also, to obtain perfluorinated trialkylamines of higher boiling points, longer alkyl chains are required in the precursor trialkylamines. However, such higher molecular weight trialkylamines give lower yields in the electrochemical fluorination process than the lower molecular weight trialkylamines.

Fluorinated aminoether compounds having amino nitrogen and side chains containing ether bonds are disclosed in U.S. Pat. No. 3,882,178 (Benninger et al.), U.S. Pat. No. 3,882,182 (Benninger et al.), U.S. Pat. No. 3,891,625 (Benninger et al.) and U.S. Pat. No. 3,997,609 (Martini et al.).

U.S. Pat. No. 3,997,609 discloses partially fluorinated aminoethers prepared by reacting tertiary amines having hydroxyethyl or 2-hydroxypropyl groups with hexafluoropropene to obtain the hexafluoropropyl ether of the tertiary amine.

U.S. Pat. No. 3,882,178 discloses fluorinated tertiary amino ethers containing ether bonds in side chains prepared by reacting fluorine-free amino alcohol or alcoholate with tetrafluoroethylene, then electrochemically fluorinating the resulting compound.

U.S. Pat. No. 3,882,182 discloses tertiary perfluoroaminoethers containing ether bonds in side chains prepared by reacting fluorine-free amino alcohols or alcoholates with hexafluoropropene to obtain tertiary hexafluoropropoxyalkyl amines, then electrochemically fluorinating the tertiary hexafluoropropoxyalkyl amine.

U.S. Pat. No. 3,891,625 discloses tertiary perfluoroaminoethers containing ether bonds in side chains prepared by introducing oxyethyl or oxypropyl groups into an oligomeric amine, e.g., by reaction with ethylene oxide, propylene oxide, or 3-chloro-1-propanol, completely etherifying the oxyalkylated amine with tetrafluoroethylene or hexafluoropropylene, then electrochemically fluorinating the etherified amine.

U.S. Pat. No. 3,274,081 and T. Ono et al., J Fluorine Chem., 27, 333 (1985) disclose improved yields of perfluorinated organic compounds using partially fluorinated starting materials in the electrochemical fluorination process.

This invention provides, in one aspect, perfluorinated aminoether compositions comprising perfluoroaminoether compounds having 2 or more, preferably 2 or 3, tertiary amino nitrogen atoms each of which is connected to the other(s) adjacent thereto by (1) a catenary, ether oxygen-containing, perfluoroalkylene linking group, such as —C$_2$F$_4$—O—C$_2$F$_4$— and —C$_2$F$_4$OC$_2$F$_4$OC$_2$F$_4$—, the catenary carbon atoms of which are in the form of perfluoroalkylene segments of vicinal carbon atoms that are two to four in number, said segments having up to 5 carbon atoms, (2) a catenary ether oxygen-containing perfluorocyclohexylene linking group, such as

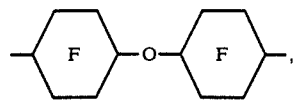

of (3) a catenary ether oxygen-containing linking group having said perfluoroalkylene segments and perfluorocyclohexylene moieties, such as

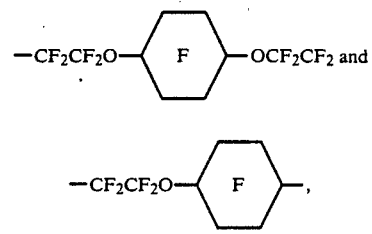

the sum of the catenary ether oxygen atoms in said linking groups being 1 to 6, and said perfluoroaminoether compounds preferably having 10 to 24, and as many as 30 or more carbon atoms.

This invention further provides a process for preparing the perfluorinated aminoether compositions of the invention.

The perfluorinated aminoether compositions of this invention (hereinafter frequently referred to for purposes of brevity, as perfluoroaminoethers) generally are normally liquid, have a wide liquid range, including boiling points up to about 300° C. or higher, e.g., 400° C., and pour points as low as −90° C., and have utility as hydraulic fluids, heat transfer fluids, pump fluids for corrosive environments, and fluids for vapor phase condensation heating for soldering and polymer curing applications.

The perfluoroaminoether compositions of the present invention are preferably prepared by electrochemical fluorination of fluorine-free precursor aminoethers which are analogous to the desired perfluoroaminoether. Electrochemical fluorination of fluorine-free precursor aminoethers provides an economical process for preparing the perfluoroaminoethers of the invention. In some cases, the perfluoroaminoethers of this invention can also be prepared by electrochemical fluorination of partially fluorinated precursor aminoethers, but this method is generally more costly. By proper selection of the precursor aminoether compounds, particularly surprisingly high yields, as high as fifty percent or more, based on current consumed in the electrofluorination, for perfluoroaminoethers having as many as 16 to 24 or 30 or more carbon atoms can be obtained. Precursor aminoether compounds having the nitrogen and oxygen atoms connected by acyclic alkylene groups having 2 to 4 carbon atoms and/or arylene groups having up to 8 carbon atoms are preferred.

A preferred class of the perfluoroaminoethers of this invention is that represented by the general formula I

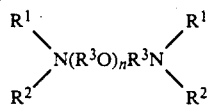

where each $R^1$ and $R^2$ are independently selected from perfluoroalkyl radicals having one to six carbon atoms, or the $R^1$ and $R^2$ are perfluoroalkyl radicals which together with the nitrogen atom to which they are bonded form a 5- or 6-member ring which may be substituted with one or more $CF_3$—, $C_2F_5$—, or $C_3F_7$— ring substituents and may contain ether oxygen or additional tertiary amino nitrogen as ring atoms, e.g. rings, such as

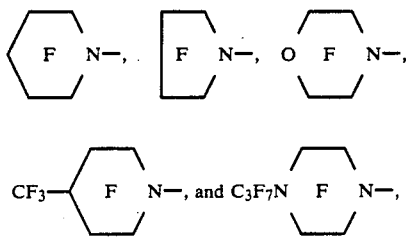

preferably

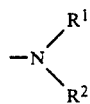

is selected from

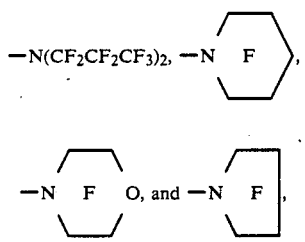

each $R^3$ is independently selected from acyclic perfluoroalkylene groups having 2 to 5 carbon atoms, at least 2 of which are vicinal, catenary atoms, and perfluorocyclohexylene groups optionally substituted with one or more of $CF_3$—, $C_2F_5$—, and $C_3F_7$— substituents, representative examples of $R^3$ being —$CF_2CF_2$—, —$CF_2CF_2CF_2$—, —$CF_2CF_2CF_2CF_2$—, —$CF_2CF(CF_3)$—, —$CF(CF_3)CF_2$—,

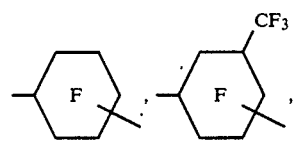

—$CF_2CF(C_2F_5)$—, $CF(C_2F_5)CF_2$—, and —$CF_2C(CF_3)_2CF_2$—, and preferably —$CF_2CF_2$—, —$CF_2CF(CF_3)$—, or —$CF(CF_3)CF_2$—, and n is an integer of 1 to 3.

Another class of the perfluoroaminoethers of this invention is that represented by the general Formula II

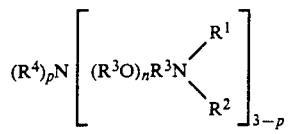

Where $R^1$, $R^2$, $R^3$ and n are as defined above for I, $R^4$ is a perfluoroalkyl radical having one to six carbon atoms or a perfluorocyclohexyl radical optionally substituted with $CF_3$— or $C_2F_5$— and p is 0 or 1.

The precursor aminoethers for the preparation of the perfluoroaminoethers of this invention can be prepared by utilizing known organic reaction techniques. An especially useful ether synthesis for that purpose, utilizing a phase transfer catalyst, i.e., a quaternary ammonium salt, is described by H. H. Freedman and R. A. Dubois in *Tetrahedron Letters*, pages 3251-4 (1975), which description is incorporated herein by reference. An adaptation of such synthesis which can be utilized to prepare said precursor aminoethers is the condensation of hydroxy group-containing tertiary amines with chloroalkylene tertiary amines. The precursor aminoethers can also be prepared by the condensation of chloroalkylene tertiaryamines and alpha, omega diols. The precursor aminoethers can contain unsaturation. For example, olefinic, acetylenic, or aromatic moieties may be present. The resulting aminoethers are preferred electrochemical fluorination starting materials to prepare the perfluoroaminoethers of this invention because of ease of preparation and/or improved electrochemical fluorination yields. Specific examples of these syntheses of precursor aminoethers are shown in Schemes 1, 2. 3, and 4. Other useful routes to precursor aminoethers are condensation of secondary amines with chloroalkylene ethers, as shown in Scheme 5, condensation of chloroalkylene tertiary amines with partially fluorinated aliphatic diols, as shown in Scheme 6 condensation of chloroalkylene ethers with unsaturated secondary amines, as shown in Scheme 7, and condensation of chloroalkylene tertiary amines with hydroxyalkylene tertiary amines to yield complex mixtures as shown in Scheme 8.

Scheme 1

Scheme 2

Scheme 3

Scheme 4

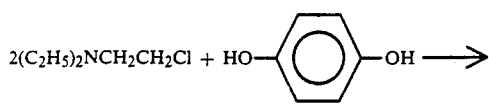

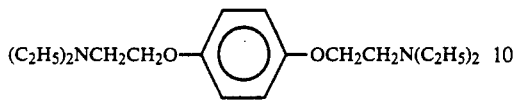

Scheme 5

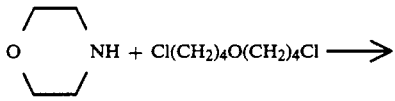

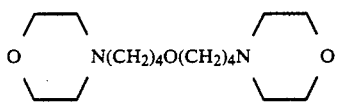

Scheme 6

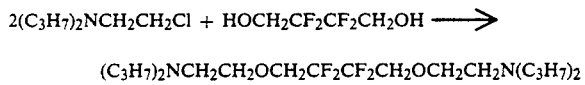

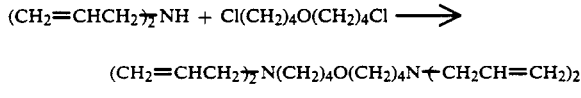

Scheme 7

(CH$_2$=CHCH$_2$)$_2$NH + Cl(CH$_2$)$_4$O(CH$_2$)$_4$Cl ⟶

(CH$_2$=CHCH$_2$)$_2$N(CH$_2$)$_4$O(CH$_2$)$_4$N(CH$_2$CH=CH$_2$)$_2$

Scheme 8

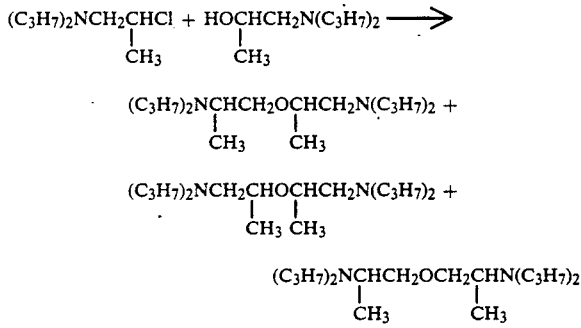

Briefly, the perfluorinated aminoether compositions of this invention can be prepared by electrochemically fluorinating aminoether precursors having 2 or more, preferably 2 or 3, tertiary amino nitrogen atoms each of which is connected to the other(s) adjacent thereto by (1) a catenary, ether oxygen-containing, aliphatic linking group such as —C$_2$H$_4$—O—C$_2$H$_4$—, —C$_2$H$_4$—O—C$_2$H$_4$—O—C$_2$H$_4$— and —CH$_2$CH$_2$OCH$_2$C≡CCH$_2$OCH$_2$CH$_2$— the catenary carbon atoms of which are in the form of segments of vicinal carbon atoms that are 2 to 4 in number, said segments having up to 5 carbon atoms, (2) a catenary ether oxygen-containing cyclohexylene or phenylene linking group, such as

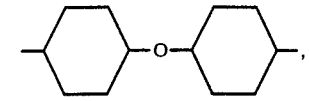

or (3) a catenary ether oxygen-containing linking group having alkylene and cyclohexylene or phenylene moieties, such as

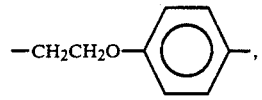

the sum of the catenary ether oxygen atoms being 1 to 6, and said precursor preferably having 10 to 24 or 30 or higher carbon atoms.

Subclasses of aminoether precursors that can be electrochemically fluorinated are those which can be represented by formulas like formulas I and II except that R$^1$ and R$^2$ are aliphatic, R$^3$ and R$^4$ are aliphatic, i.e., in the case of R$^3$, alkylene or cyclohexylene, and R$^4$ alkyl, alkenyl, alkynyl, cyclohexyl, or phenyl and any of R$^1$, R$^2$, R$^3$, and R$^4$ can be partially halogenated, though preferably are halogen-free and is preferably R$^4$ alkyl phenyl.

Scheme 9 illustrates the electrochemical fluorination of the product of Scheme 1 to yield a perfluorinated aminoether of this invention. The products of Schemes 2-8 can be electrochemically fluorinated in a similar manner to yield the corresponding perfluoroaminoethers of this invention.

Scheme 9

(C$_3$F$_7$)$_2$NC$_2$F$_4$OC$_2$F$_4$N(C$_3$F$_7$)$_2$

The conversion of organic compounds to perfluorinated derivatives by electrochemical fluorination is described, for example, in U.S. Pat. No. 2,519,983 (Simons) and U.S. Pat. No. 2,567,011 (Simons et al.). The precursor aminoethers may also be electrochemically fluorinated using organic conductivity additives as described in U.S. Pat. No. 3,028,321 (Danielson). Thus, further details on the reparation of the perfluoroaminoethers of this invention by electrochemical fluorination will be omitted in the interest of brevity and these patents are incorporated herein by reference for such details.

As is well known, the liquid electrochemical fluorination process produces product mixtures of perfluorinated materials related to the original organic precursor skeletal structure, resulting from one or more isomerization, cleavage, or recombination reactions. Thus, in a boiling range corresponding to the desired product, it is usual to find a host of related perfluorinated compounds. Generally, separation and/or identification of these compounds is extremely difficult and not necessary to the use of the products. Generally, the desired perfluoroaminoether material comprises the major component, and usually the predominant component, e.g. as high as 90 weight percent or more of the product mixture, indicating the unusually favorable electrochemical fluorination behavior of the aminoether precursors. In some cases considerable structural reorganization of the precursor occurs during fluorination, as indicated by boiling points both lower and higher than expected and by fluorine nuclear magnetic reasonance, F-nmr, and gas chromatography-mass spectrometry, gc-ms, analyses. Materials of $C_{18}$ and $C_{20}$ content might be expected to have boiling points of 250°–270° C. and 270°–300° C., respectively. However, some of the higher molecular weight materials do not have as high a carbon content as the precursors. Lower molecular weight cleavage products also may be useful perfluorinated aminoether compositions of this invention.

The perfluoroaminoether compositions can contain a small amount of hydrogen due to incomplete fluorination. The amount of hydrogen retained generally ranges from less than 0.005 mg/g to as much as 1.5 mg/g with most perfluoroaminoethers containing less than 0.3 mg/g. The hydrogen atoms generally tend to group rather than be randomly distributed as suggested by gc-ms analyses of compounds showing two and four hydrogen atoms. Purification of the product, i.e. removal of partially fluorinated products and carboxylic acid fluoride by-product, can be carried out, for example, by boiling the product with aqueous alkaline solution, a well-known technique in the art.

The alkali-purified perfluorinated aminoether products contain minor or very small amounts of heat-labile materials, such as isomers or homologs. Upon prolonged exposure to elevated temperatures, i.e., reflux temperatures, these heat-labile materials decompose to products which on contact with atmospheric moisture produce HF. Such materials can cause metal corrosion and, at sufficiently high temperatures, may preclude use of the aminoether as an inert heat exchange fluid. Surprisingly, it has been found that a substantial reduction of the minor amounts of the HF-producing products can be achieved by heating the perfluorinated aminoether products at a sufficiently high temperature for a sufficient period of time. The use of higher temperatures reduces the amount of time required to remove the heat-labile materials. Generally, a sufficient amount of the heat-labile materials can be removed by heating for 20 to 60 minutes at a temperature about 100° C. above the intended application temperature of the perfluorinated aminoether product. Healing at a temperature 50° C. above the intended application temperature may require a 4-hour treatment period. Heating at a temperature only 20° C. above the intended application temperature can require a treatment period of as long as 24 hours or more. At temperatures less than about 20° C. above the elevated application temperature, insufficient heat-labile materials are removed to adequately reduce HF formation. At temperatures greater than about 100° C. above the elevated application temperature, little additional heat-labile materials are removed.

Certain of the cyclic symmetrical perfluoroaminoethers formed crystalline solids on cooling below normal or ambient temperatures, rather than the low-temperature glasses formed by most perfluoroaminoethers of this invention, although they possess good fluidity above the crystallization temperature. Blending such crystalline perfluoroaminoethers with other perfluoroaminoethers generally results in compositions having lower pour points.

Useful aminoether precursor compounds for conversion to the perfluorinated aminoether compositions of this invention by electrochemical fluorination include the following compounds:

Monoethers
2-(dimethylamino)ethyl 2-(piperidino)ethyl ether
bis[(2-diethylamino)ethyl] ether
bis[(2-morpholino)ethyl] ether
bis[(2-pyrrolidino)ethyl] ether
2-(diethylamino)ethyl 2-(morpholino)ethyl ether
2-(morpholino)ethyl 1-(morpholino)-2-propyl ether
2-(morpholino)ethyl 2-(morpholino)-1-propyl ether
2-(diethylamino)ethyl 2-(dipropylamino)ethyl ether
2-(dipropylamino)ethyl 2-(morpholino)ethyl ether
2-(diethylamino)ethyl 2-(N-methylanilino)ethyl ether
bis[(2-piperidino)ethyl] ether
2-(dipropylamino)ethyl 1-(morpholino)-2-propyl ether
bis[(2-dipropylamino)ethyl] ether
bis[(2-diisopropylamino)ethyl] ether
1-(dipropylamino)-2-propyl 2-(piperidino)ethyl ether
2-(diethylamino)ethyl 2-(dibutylamino)ethyl ether
bis[(4-diethylamino)butyl] ether
bis[(4-morpholino)butyl] ether
2-(diethylamino)ethyl 3-(diethylamino)phenyl ether
bis[(3-dipropylamino)propyl] ether
1-(dipropylamino)-2-propyl 2-(dipropylamino)-1-propyl ether
bis[(4-(2,'6'-dimethyl)morpholino)butyl] ether
bis[(4-dipropylamino)butyl] ether
bis[(4-diethylamino)phenyl] ether Diethers, triethers
1,2-bis[(2-morpholino)ethoxy]ethane
1,4-bis[(2-diethylamino)ethoxy]butane
1,4-bis[(2-diethylamino)ethoxy]-2-butyne
1,4-bis[(2-morpholino)ethoxy]-2-butyne
1,2-bis[(2-piperidino)ethoxy]ethane
bis[(2-diethylamino)ethoxyethyl] ether
2,2-dimethyl-1,3-bis[(2-diethylamino)ethoxy]propane
N-methyl-N,N-bis[(2-diethylamino)ethoxyethyl]amine
1,2-bis[(2-dipropylamino)ethoxy]ethane
1,2-bis[(2-diethylamino)ethoxy]benzene
1,3-bis[(2-diethylamino)ethoxy]benzene
1,4-bis[(2-diethylamino)ethoxy]benzene Many of the perfluorinated aminoether compositions of this invention have desirably low pour points compared with perfluorotrialkylamines having the same number of carbon atoms. For example, $C_6F_{13})_3N$ having 18 carbon atoms is a semi-solid at room temperature, while $(C_3F_7)_2NCF_2CF_2CF_2OCF_2CF_{2CF_2}N(C_3F)_2$ also containing 18 carbon atoms, and therefore having about the same boiling range, has a pour point of $-45°$ C. These low pour points, manifested by good fluidity at low temperature, coupled with high boiling points for many of the perfluorinated aminoether compositions of this invention, generally have utility in many applications where this broad fluid range, and other properties of these fluids, e.g., non-flammability and chemical stability, are desired or needed. Such applications include, for example, hydraulic fluids, pump fluids for corrosive environments, heat transfer fluids, and vapor phase (or condensation) heating for soldering and polymer curing applications.

This invention is further illustrated by the following examples, but the particular materials and amounts thereof recited in these examples, as well as other conditions and details, should not be construed to unduly limit this invention. In the following examples, the propyl and butyl groups are n-propyl and n-butyl groups unless otherwise indicated.

EXAMPLE 1

Bis[2-(dipropylamino)ethyl] ether precursor was prepared from 2-(dipropylamino)ethanol and 2-(dipropylamino)ethyl chloride in tetrahydrofuran solution by heating in the presence of aqueous sodium hydroxide acid acceptor and a small amount of ADOGEN 464 quaternary ammonium salt catalyst, and isolating the aminoether precursor from the organic phase by water washing and distillation at a boiling range of 120°–125° C. at 0.5 torr.

A 100 ampere electrochemical cell of the type described in U.S. Pat. No. 2,713,593 was charged with 2300 g anhydrous liquid hydrogen fluoride. A solution of 2100 g of the bis[2-(dipropylamino)ethyl] ether in 955 g anhydrous liquid hydrogen fluoride was added periodically over a period of 269 hours to the cell, along with additional hydrogen fluoride as needed to replace that consumed in the reaction and lost through the condensing system. The cell was operated continuously at an average of about 6 volts, 60 amps, 55° C. and 30 psig (0.207 MPa). The perfluorinated liquid product mixture was recovered as the lower phase from the liquid hydrogen fluoride present in the condensing system trap and in the cell itself to give a total of 5120 g of crude product. The crude product was treated with sodium fluoride to remove hydrogen fluoride, filtered and distilled to yield a total of 3900 g (52% current yield, 55% organic yield) of a main cut boiling in the range of 225°–240° C. After treatment with caustic, F-nmr analysis indicated the presence of over 90% of the desired product, mainly $(CF_3CF_2CF_2)_2NCF_2CF_2OCF_2CF_2N(CF_2CF_2CF_3)_2$. Gc-ms indicated 85% of this material, the remainder consisting of the parent compound minus one and two $CF_2$ groups from the terminal propyl groups.

The pour point was estimated to be $-55°$ to $-60°$ C. by cooling a sample of the distilled liquid product to a solid, glassy state in a glass vial, having a thermometer, immersed in the liquid, in a liquid nitrogen bath, and allowing to warm slowly and noting the temperature at which complete fluidity is attained.

EXAMPLES 2–7

Following the procedure of Example 1, aminoethers were fluorinated by electrochemical fluorination and isolated. The presence of the principal perfluoroaminoether, as determined by F-nmr analysis, and, for most materials, the boiling range, % yield, and pour points using the procedure of Example 1 are set forth in Table 1.

TABLE 1

| Example | Perfluoroaminoether | Boiling Range (°C.) | Pour Point (°C.) | Yield (wt. %) |
|---|---|---|---|---|
| 2 | $(CF_3)_2NCF_2CF_2OCF_2CF_2N$(piperidinyl-F) | 143–167 | −90 | 6 |
| 3 | $(C_2F_5)_2NCF_2CF_2OCF_2CF_2N(C_2F_5)_2$ | 178–180 | −80 | 23 |
| 4 | $O$(morpholinyl-F)$NCF_2CF_2OCF_2CF_2N$(morpholinyl-F)$O$ | 175–185 | −5 | 44 |
| 5 | $(C_3F_7)_2NCF_2CF_2OCF_2CF_2N(C_3F_7)_2$ | 225–240 | −60 | 52 |
| 6 | $(C_2F_5)_2NCF_2CF_2OCF_2CF_2N(C_4F_9)_2$ | 215–230 | −50 | 32 |
| 7 | $[(C_2F_5)_2NCF_2CF_2OCF_2CF_2]_2NCF_3$ | —* | — | 4 |

*not evaluated

EXAMPLES 8–23

In Examples 8–23, aminoethers were fluorinated by electrochemical fluorination and isolated as in Example 1 except the cell temperature was 50° C. The structure of the principal perfluoroaminoether, the boiling range, the pour point, and the yield are set forth in Table 2.

TABLE 2

| Example | Perfluoroaminoether | Boiling Range (°C.) | Pour Point (°C.) | Yield (wt. %) |
|---|---|---|---|---|
| 8 | F(piperidinyl)$NCF_2CF_2OCF_2CF_2N$(piperidinyl)F | 170–185 | −85 | 40 |
| 9 | O(morpholinyl)F $NCF_2CF_2OCFCF_2N$(morpholinyl)F O, with $CF_3$ branch | 198–206 | −60 | 41 |
| 10 | O(morpholinyl)F $NCF_2CF_2OCF_2CFN$(morpholinyl)F O, with $CF_3$ branch | 198–200 | −70 | 35 |

TABLE 2-continued

| Example | Perfluoroaminoether | Boiling Range (°C.) | Pour Point (°C.) | Yield (wt. %) |
|---|---|---|---|---|
| 11 | (C₃F₇)₂NCF₂CF₂OCF₂CF₂N⟨F⟩O (morpholine ring) | 195–215 | −65 | 42 |
| 12 | (C₂F₅)₂NCF₂CF₂OCF₂CF₂N—⟨F⟩ with CF₃ substituent | 195–230 | −70 | 4 |
| 13 | ⟨F⟩N—CF₂CF₂OCF₂CF₂N—⟨F⟩ | 207–219 | −10 | 45 |
| 14 | (i-C₃F₇)₂NCF₂CF₂OCF₂CF₂N(i-C₃F₇)₂ | — | — | 5 |
| 15 | (C₃F₇)₂N(CF₂)₃O(CF₂)₃N(C₃F₇)₂ | 240–265 | −45 | 18 |
| 16 | (C₃F₇)₂N(CF₂)₄O(CF₂)₄N(C₃F₇)₂ | 240–260 | — | 7 |
| 17 | (C₂F₅)₂NCF₂CF₂OCF₂CF₂N(C₃F₇)₂ | 195–200 | −75 | 33 |
| 18 | O⟨F⟩NCF₂CF₂OCF₂CF₂OCF₂CF₂N⟨F⟩O | 200–215 | −10 | 15 |
| 19 | ⟨F⟩NCF₂CF₂OCF₂CF₂OCF₂CF₂N⟨F⟩ | 220–240 | −65 | 17 |
| 20 | [(C₂F₅)₂NCF₂CF₂OCF₂CF₂]₂O | — | — | 8 |
| 21 | (C₂F₅)₂NCF₂CF₂OCF₂C(CF₃)₂—CF₂OCF₂CF₂N(C₂F₅)₂ | — | — | 5 |
| 22 | (C₃F₇)₂NCF₂CF₂OCF₂—CF₂OCF₂CF₂N(C₃F₇)₂ | 255–285 | −65 | 10 |
| 23 | ⟨F⟩NCF₂CF₂OCF₂CF₂CF₂—OCF₂CF₂N⟨F⟩ | 210–260 | −30 | 4 |

EXAMPLES 24–28

In Examples 24–28, aminoethers were fluorinated by electrochemical fluorination and isolated as in Example 1, except the cell temperature was 20° C. in Examples 24–27 and 45° C. in Example 28. The structure of the principal perfluoroaminoether, the boiling range, pour point, and yield are set forth in Table 3.

TABLE 3

| Example | Perfluoroaminoether | Boiling Range (°C.) | Pour Point (°C.) | Yield (wt. %) |
|---|---|---|---|---|
| 24 | (C₃F₇)₂NCF₂CF₂OCFCF₂N⟨F⟩O with CF₃ substituent | — | — | 38 |

TABLE 3-continued

| Example | Perfluoroaminoether | Boiling Range (°C.) | Pour Point (°C.) | Yield (wt. %) |
|---|---|---|---|---|
| 25 | (C$_3$F$_7$)$_2$NCF$_2$CFOCF$_2$CF$_2$N⟨C$_6$F$_{10}$O⟩<br>　　　　　　　　｜<br>　　　　　　　　CF$_3$ | 215–225 | −60 | 19 |
| 26 | (C$_3$F$_7$)$_2$NCF$_2$CFOCF$_2$CFN(C$_3$F$_7$)$_2$ (major)<br>　　　　　　｜　　　　｜<br>　　　　　　CF$_3$　　CF$_3$<br><br>(C$_3$F$_7$)$_2$NCF$_2$CFOCFCF$_2$N(C$_3$F$_7$)$_2$<br>　　　　　　｜　｜<br>　　　　　　CF$_3$ CF$_3$<br><br>(C$_3$F$_7$)$_2$NCFCF$_2$OCF$_2$CFN(C$_3$F$_7$)$_2$<br>　　　　　｜　　　　　｜<br>　　　　　CF$_3$　　　　CF$_3$ | 250–275 | −40 | 33 |
| 27 | CF$_3$-⟨O,F,N⟩(CF$_2$)$_4$O(CF$_2$)$_4$N⟨F,O⟩-CF$_3$ (bis-morpholine structure with CF$_3$ substituents) | 240–265 | −25 | 10 |
| 28 | (C$_2$F$_5$)$_2$NCF$_2$CF$_2$OCF$_2$CF$_2$N⟨F,O ring⟩ | 175–185 | −80 | 39 |

EXAMPLES 29–34

In Examples 29–34, aminoethers were fluorinated by electrochemical fluorination and isolated as in Example 1, except using cell temperatures of 50° C. in Examples 29–32, 55° C. in Example 33, and 35° C. in Example 34 and adding ten weight percent dimethyl disulfide based on the weight of the aminoether to the system as taught in U.S. Pat. No. 3,028,321. The structure of the principal perfluoroaminoether, the boiling range, pour point, and yield are set forth in Table 4.

TABLE 4

| Example | Perfluoroaminoether | Boiling Range (°C.) | Pour Point (°C.) | Yield (wt. %) |
|---|---|---|---|---|
| 29 | (C$_2$F$_5$)$_2$N(CF$_2$)$_4$O(CF$_2$)$_4$N(C$_2$F$_5$)$_2$ | 200–210 | — | 19 |
| 30 | (C$_2$F$_5$)$_2$NCF$_2$CF$_2$O—⟨C$_6$F$_{10}$⟩—N(C$_2$F$_5$)$_2$ | 210–225 | −40 | 18 |
| 31 | ⟨O,F ring⟩NCF$_2$CF$_2$OCF$_2$CF$_2$—<br>　　—CF$_2$CF$_2$OCF$_2$CF$_2$N⟨F,O ring⟩ | 224–230 | — | 5 |
| 32 | (C$_2$F$_5$)$_2$NCF$_2$CF$_2$O—⟨C$_6$F$_{10}$⟩—OCF$_2$CF$_2$N(C$_2$F$_5$)$_2$ | 220–250 | −55 | 22 |
| 33 | (C$_2$F$_5$)$_2$NCF$_2$CF$_2$O—⟨C$_6$F$_{11}$⟩ | 200–220 | — | 20 |

TABLE 4-continued

| Example | Perfluoroaminoether | Boiling Range (°C.) | Pour Point (°C.) | Yield (wt. %) |
|---|---|---|---|---|
| | —OCF$_2$CF$_2$N(C$_2$F$_5$)$_2$ | | | |
| 34 | (C$_2$F$_5$)$_2$NCF$_2$CF$_2$OCF$_2$CF$_2$—<br>—CF$_2$CF$_2$OCF$_2$CF$_2$N(C$_2$F$_5$)$_2$ | 200–240 | −70 | 15 |

EXAMPLES 35 AND 37

In Examples 35–37, aminoethers were fluorinated by electrochemical fluorination and isolated as in Example 1, except in Examples 35 and 36 the cell temperature was 50° C. and 20 weight percent dimethyl disulfide based on the weight of the aminoether was added at the beginning of the reaction and was gradually reduced to zero and in Example 37 the cell temperature was 35° C. and 10 weight percent dimethyl disulfide based on the weight of the aminoether was added throughout the reaction. The structure of the principal perfluoroaminoether, the boiling range, pour point, and yield are set forth in Table 5.

TABLE 5

| Example | Perfluoroaminoether | Boiling Range (°C.) | Pour Point (°C.) | Yield (wt. %) |
|---|---|---|---|---|
| 35 | 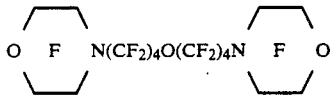 O  F  N(CF$_2$)$_4$O(CF$_2$)$_4$N  F  O | 200–235 | 0 | 23 |
| 36 | [(C$_2$F$_5$)$_2$N—⟨F⟩—]$_2$O | 220–260 | −30 | 7 |
| 37 | (C$_2$F$_5$)$_2$NCF$_2$CF$_2$O—⟨F⟩—<br>—OCF$_2$CF$_2$N(C$_2$F$_5$)$_2$ | 200–250 | −45 | 22 |

EXAMPLES 38 AND 39

In Example 38, a mixture of 50 weight percent of the perfluoroaminoether of Example 3, (C$_2$F$_5$)$_2$NCF$_2$CF$_2$OCF$_2$CF$_2$N(C$_2$F$_5$)$_2$, having a boiling range of 178°–180° C. and a pour point of −80° C., and 50 weight percent of the perfluoroaminoether of Example 4,

O  F  NCF$_2$CF$_2$OCF$_2$CF$_2$N  F  O, having a boiling range of 175°–185° C. and a pour point, or crystallization temperature, of −5° C, was prepared. The boiling range of the mixture was 175°–185° C. The pour point of the mixture was −70° C., a value much closer to the pour point of the perfluoroaminoether of Example 3 than to the pour point of the perfluoroaminoether of Example 4.

In Example 39 a mixture of 50 weight percent of the perfluoroaminoether of Example 18,

O  F  NCF$_2$CF$_2$OCF$_2$CF$_2$OCF$_2$CF$_2$N  F  O, having a boiling range of 200°–215° C. and a pour point, or crystallization temperature, of −10° C., and 50 weight percent of the perfluoroaminoether of Example 19,

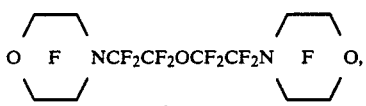
⟨F  NCF$_2$CF$_2$OCF$_2$CF$_2$OCF$_2$CF$_2$N  F⟩, having a boiling range of 220°–240° C. and a pour point of −65° C., was prepared. The boiling range of the mixture was 200°–240° C. The pour point of the mixture was −50° C., a value much closer to the pour point of the perfluoroaminoether of Example 19 than to the pour point of the perfluoroaminoether of Example 18.

Examples 38 and 39 demonstrate that the utility of the perfluoroaminoethers having high pour points can be increased by mixing with perfluoroaminoethers having low pour points, the pour point of the mixture being only slightly increased from that of the lower pour point perfluoroaminoether.

EXAMPLE 40

Bis[2-(dihexylamino)ethyl]ether was fluorinated by electrochemical fluorination at a cell temperature of 20° C. The principle perfluoroaminoether product, [(n—C$_6$F$_{13}$)$_2$NFC$_2$CF$_2$]$_2$O, had a boiling range of 160°–180° C./0.4 torr and a pour point of 10° C. The yield was 15 percent.

EXAMPLE 41

N,N-Bis[dipropylaminoethoxyethyl]-N-propylamine was fluorinated by electrochemical fluorination at a cell temperature of 20° C. The principal perfluoroaminoether product, [(n—C$_3$F$_7$)$_2$NCF$_2$CF$_2$OCF$_2$CF$_2$]$_2$N—n—C$_3$F$_7$, had a boiling range of 160°-190° C./26 torr and a pour point of −25° C. The yield was 25 percent.

EXAMPLE 42

Dipentylaminoethyldipropylaminoethylether was fluorinated by electrochemical fluorination at a cell temperature of 20° C., treated with sodium fluoride and distilled. The principal product, (C$_5$F$_{11}$)$_2$NCF$_2$CF$_2$OCF$_2$CF$_2$N(C$_3$F$_7$)$_2$, had a boiling point of 92°-94° C./0.1 torr and a pour point of −30° C. The yield was 26%.

EXAMPLE 43

Tris(dipropylaminoethoxyethyl)amine was fluorinated by electrochemical fluorination at a cell temperature of 20° C. The principal product, [(C$_3$F$_7$)$_2$NCF$_2$CF$_2$OCF$_2$CF$_2$—]$_3$N, had a boiling point of 220° C./0.2 torr and a pour point of 0° C. The yield was 12%.

EXAMPLE 44

Bis-dipentylaminoethylether was fluorinated by electrochemical fluorination at a cell temperature of 20° C. The principal product, [(C$_5$F$_{11}$)$_2$NCF$_2$CF$_2$]$_2$O, had a boiling point of 130° C./0.15 torr and a pour point of −25° C. The yield was 30%.

EXAMPLE 45

Following the procedure of Example 1, di-n-butylaminoethyl di-n-propylaminoethyl ether was fluorinated by electrochemical fluorination at a cell temperature of 55° C., treated with sodium fluoride, and distilled to yield a product having a boiling range of 240° to 260° C. The yield was 30%. The product was treated with caustic and potassium permanganate to yield a material containing 91% of the desired product, [CF$_3$(CF$_2$)$_3$]$_2$NFC$_2$CF$_2$OCF$_2$CF$_2$N[(CF$_2$)$_2$CF$_3$]$_2$. The fluorinated material had a boiling range of 243° to 255° C. and a pour point of −40° C. A 5 g portion of the fluorinated material and 15 g of 0.1M aqueous potassium hydroxide were heated at 250° C. for 22 hours. The hydrogen fluoride content of the resulting mixture was found to be 43 μg/g-hour.

In a Parr reactor, 175 g of the fluorinated material was heated at 350° C. for 1 hour at a maximum pressure of 100 psi (690 kPa). At the completion of this heat treatment, 96% of the material was recovered. This heat-treated material was distilled, treated with potassium permanganate. dried with silica gel, to yield stabilized [CF$_3$(CF$_2$)$_3$]$_2$NCF$_2$CF$_2$OCF$_2$CF$_2$N](CF$_2$)$_2$CF$_3$]$_2$. This stabilized product had a boiling point of 250° C., a pour point of −45° C. Upon refluxing under nitrogen atmosphere, 0.001 μg/g-hour perfluoroisobutylene evolved as determined by gc analysis of the nitrogen-swept head space. A 5 g portion of the heat-treated material and 15 g of 0.1M aqueous potassium hydroxide were heated for 22 hours at 250° C. The hydrogen fluoride content of the resulting mixture was 17.7 μg/g-hour.

The various modifications and alterations of this invention will be apparent to those skilled in the art without departing from the scope and spirit of this invention and this invention should not be restricted to that set forth herein for illustrative purposes.

We claim:

1. Perfluoroaminoethers having two or more tertiary amino nitrogen atoms each of which is connected to the other(s) adjacent thereto by (1) a catenary, ether oxygen-containing, perfluoroalkylene linking group the catenary carbon atoms of which are in the form of perfluoroalkylene segments of vicinal carbon atoms that are 2 to 3 in number, said segments having up to 5 carbon atoms, (2) a catenary ether oxygen-containing perfluorocyclohexylene linking group, or (3) a catenary ether oxygen-containing linking group having said perfluoroalkylene segments and perfluorocyclohexylene moieties, the sum of the catenary ether oxygen atoms in said linking groups being 1 to 6 and each of the terminal amino nitrogen atoms being parts of a 5- or 6-member ring, with the proviso that said ring be substituted by one or more —CF$_3$, —C$_2$F$_5$, or —C$_3$F$_7$ substituents or contain either oxygen or additional tertiary amino nitrogen as ring atoms.

2. Perfluoroaminoethers of claim 1 wherein said perfluoroaminoethers have the general formula

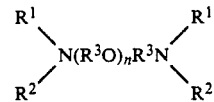

where each R$^1$ and R$^2$ are perfluoroalkyl radicals which together with the nitrogen atom to which they are bonded form a 5- or 6-member ring, with the proviso that said ring be substituted by one or more —CF$_3$, —C$_2$F$_5$, or C$_3$F$_7$ substituents or contain ether oxygen or additional tertiary amino nitrogen as ring atoms, each R$^3$ is independently selected from acyclic perfluoroalkylene groups having 2 to 5 carbon atoms at least 2 of which are vicinal, catenary atoms, and perfluorocyclohexylene, and n is 1 to 3.

3. Perfluoroaminoethers of claim 2 wherein each R$^3$ is independently selected from —CF(CF$_3$)CF$_2$—, —CF$_2$CF(C$_2$F$_5$)—, —CF(C$_2$F$_5$)CF$_2$—, —CF$_2$C(CF$_3$)$_2$CF$_2$—,

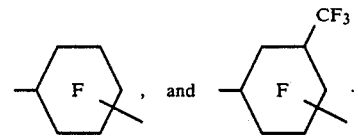

4. Perfluoroaminoethers of claim 2 wherein each R$^3$ is independently selected from —CF$_2$CF$_2$—, —CF$_2$CF(CF$_3$)— and —CF(CF$_3$)CF$_2$.

5. Perfluoroaminoethers of claim 2 wherein each

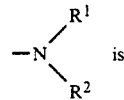

is

-continued
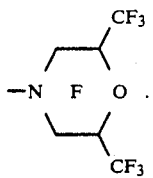
6. Perfluoroaminoethers of claim 1 wherein said perfluoroaminoether has the formula
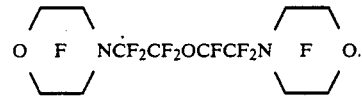
7. Perfluoroaminoethers of claim 1 wherein said perfluoroaminoether has the formula
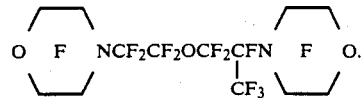
8. Perfluoroaminoethers of claim 1 wherein said perfluoroaminoether has the formula
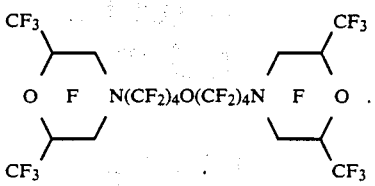
9. Perfluoroaminoethers of claim 1 wherein said perfluoroaminoether has the formula
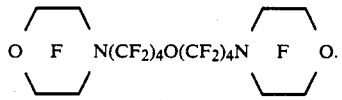
* * * * *

UNITED STATES PATENT AND TRADEMARK OFFICE
CERTIFICATE OF CORRECTION

PATENT NO. : 5,049,670
DATED : September 17, 1991
INVENTOR(S) : George G.I. Moore and John C. Hansen It is certified that error appears in the above-identified patent and that said Letters Patent is hereby corrected as shown below:

| | |
|---|---|
| Col. 4, line 27 | "tertiaryamines" should read -- tertiary amines -- |
| Col. 4, line 36 | "1, 2. 3," should read -- 1, 2, 3, -- |
| Col. 4, line 41 | "6 condensation" should read -- 6, condensation -- |
| Col. 6, line 50 | "reparation" should read -- preparation -- |
| Col. 7, line 47 | "Healing" should read -- Heating -- |
| Col. 8, line 27 | "bis[(4-(2,'6'-dimethyl)morpholino)butyl]" should read -- bis[(4-(2',6'-dimethyl)morpholino)butyl] -- |
| Col. 8, line 48 | "$(C_3F_7)_2NCF_2CF_2CF_2OCF_2CF_2CF_2N(C_3F)_2$" should read -- $(C_3F_7)_2NCF_2CF_2CF_2OCF_2CF_2CF_2N(C_3F_7)_2$ -- |

UNITED STATES PATENT AND TRADEMARK OFFICE
CERTIFICATE OF CORRECTION

PATENT NO. : 5,049,670
DATED : September 17, 1991
INVENTOR(S) : George G.I. Moore and John C. Hansen It is certified that error appears in the above-identified patent and that said Letters Patent is hereby corrected as shown below:

Col. 17, line 24  "$[(C_3F_7)_2NCF_2CF_2OCF_2CF_2\text{---}_3N$" should read
-- $[(C_3F_7)_2NCF_2CF_2OCF_2CF_2\text{-}]_3N$ --

Col. 17, line 56  "permanganate." should read
-- permanganate, --

Col. 17, line 57  "$[CF_3(CF_2)_3]_2NCF_2CF_2OCF_2CF_2N](CF_2)_2CF_3]_2.$" should read
-- $[CF_3(CF_2)_3]_2NCF_2CF_2OCF_2CF_2N[(CF_2)_2CF_3]_2.$ --

Col. 18, line 60  "$-CF(CF_3)CF_2.$" should read
-- $-CF(CF_3)CF_2-.$ --

UNITED STATES PATENT AND TRADEMARK OFFICE
CERTIFICATE OF CORRECTION

PATENT NO. : 5,049,670

DATED : September 17, 1991

INVENTOR(S) : George G.I. Moore, et al.

It is certified that error appears in the above-identified patent and that said Letters Patent is hereby corrected as shown below:

Col. 19, line 20 " 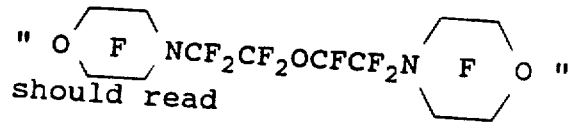 "

should read

-- 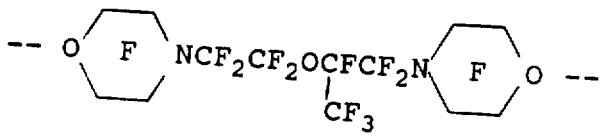 --

Signed and Sealed this

Thirty-first Day of March, 1992

Attest:

HARRY F. MANBECK, JR.

Attesting Officer

Commissioner of Patents and Trademarks